United States Patent [19]

Takayama

[11] 4,330,189
[45] May 18, 1982

[54] PHOTOGRAPHING APPARATUS FOR ENDOSCOPE

[75] Inventor: Syuichi Takayama, Hachioji, Japan

[73] Assignee: Olympus Optical Co., Ltd., Tokyo, Japan

[21] Appl. No.: 195,439

[22] Filed: Oct. 9, 1980

[30] Foreign Application Priority Data

Oct. 13, 1979 [JP] Japan ................................ 54-132002
Oct. 13, 1979 [JP] Japan ................................ 54-132003

[51] Int. Cl.³ ........................ G03B 7/00; G03B 17/18; A61B 1/04
[52] U.S. Cl. ..................................... 354/202; 354/51; 354/62; 354/289
[58] Field of Search ...................... 354/29, 30, 226, 36, 354/38, 50, 51, 60 R, 60 E, 60 L, 62, 289, 234, 235, 258, 202, 354; 128/6-9; 355/38, 71, 35-37

[56] References Cited

U.S. PATENT DOCUMENTS 3,670,722 10/1980 Kosaka ..................................... 128/6

Primary Examiner—L. T. Hix
Assistant Examiner—William B. Perkey
Attorney, Agent, or Firm—Frishauf, Holtz, Goodman and Woodward

[57] ABSTRACT

A plurality of exposure constant selection switches are provided for respectively corresponding exposure constants, and an intermediate one of these exposure constants is automatically set when none of the exposure constants are selected by selection switches. When two selection switches are operated at one time, an exposure constant corresponding to the average of the exposure constants selected by these two selection switches is automatically set.

9 Claims, 2 Drawing Figures

PHOTOGRAPHING APPARATUS FOR ENDOSCOPE

BACKGROUND OF THE INVENTION

This invention relates to photographing apparatus and, more particularly, to a photographing apparatus for an endoscope, in which an endoscope, a photographic attachment and a light source unit are used in combination to take endoscopic pictures of a body cavity.

In endoscopic photographing of a body cavity, an endoscope, a photographic attachment and a light source unit are used in combination. Usually the endoscope and photographic attachment are assembled together as a collective unit, while the light source unit, which includes switches for setting photographing data such as exposure constants and a light source, is disposed in a separate place and is connected to the endoscope and photographic attachment through a cable. Therefore, one who observes and photographs the body cavity is likely to be remiss in the operation of the light source unit since concentrated attention has to be paid for observing the body cavity when photographing it. Particularly, where a plurality of exposure constant setting switches are provided as push button switches arranged in a row, it is likely that several switch buttons are depressed at one time by mistake because the operator usually has to look at the switches at a distance and in a somewhat unnatural direction and operate them by reaching out a hand. Also, it is sometimes likely that the operation of a switch is forgotten when photographing. If several switch buttons are depressed at one time or no switch button is depressed, a proper exposure constant cannot be obtained. In such a case, proper exposure cannot be obtained, and a picture of insufficient clarity results.

Another deficiency in the endoscopic photographing apparatus using a push button switch exposure constant setting system is that only preset exposure constants are available for stepwise selection. That is, it is impossible to obtain intermediate exposure constants.

An object of the invention, accordingly, is to provide a photographing apparatus for an endoscope, with which even an erroneous operation or failure of operation of the exposure constant setting system does not result in a substantial error of a given exposure constant, and also which permits intermediate exposure constants to be obtained.

SUMMARY OF THE INVENTION

According to the invention, there is provided a photographing apparatus for endoscope, which is provided with a plurality of exposure constant setting switches for setting a desired exposure constant, and with which an intermediate one of preset exposure constants corresponding to the respective exposure constant setting switches is automatically set in the case when none of the exposure constant setting switches is operated and also an intermediate value among several ones of the preset exposure constants is automatically set when the corresponding exposure constant setting switches are operated at one time.

DETAILED DESCRIPTION

Figure 1:
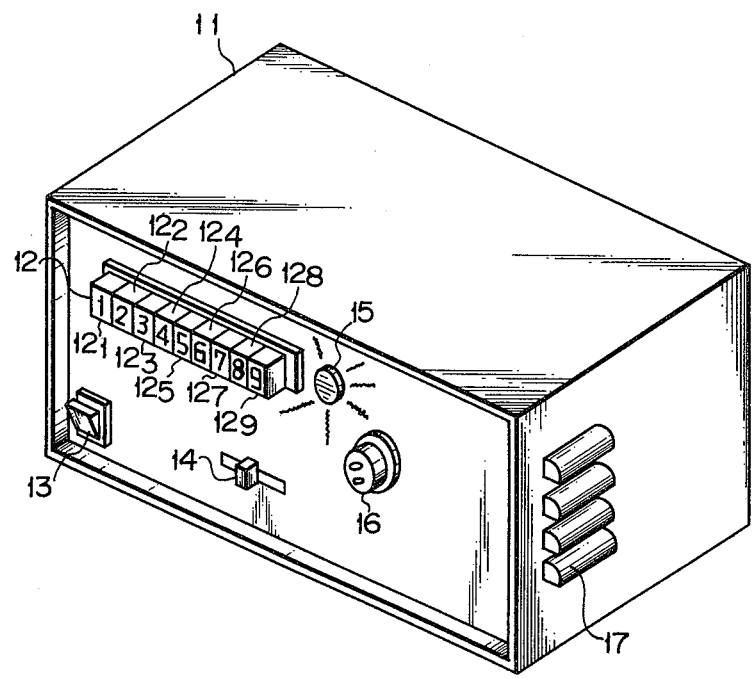
FIG. 1 is a perspective view showing a light source unit used for an embodiment of the photographing apparatus for an endoscope according to the invention.

Referring now to FIG. 1, there is shown a light source unit 11. On its front, the unit 11 has a push button panel 12 with a row of push buttons $12_1$ to $12_9$. These push buttons are provided for setting a given exposure constant for a corresponding kind of film loaded in the photographic attachment for endoscopic photographing. The light source unit 11 is also provided on the front with a power supply switch 13, a light adjusting knob 14, an alarm 15 and an output selector 16, and has ventilating holes 17 formed on one side wall.

Figure 2:
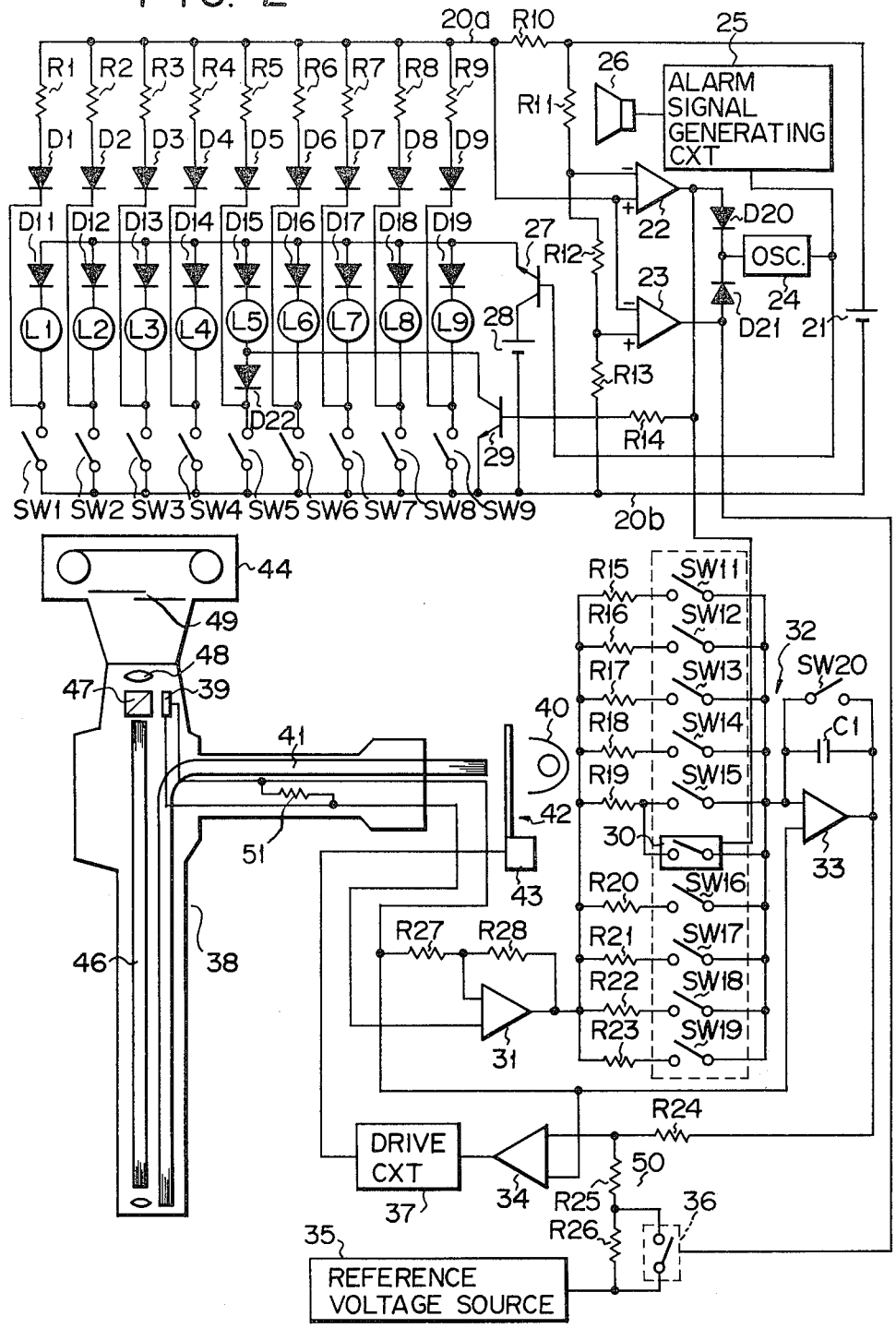
FIG. 2 is a schematic representation of the photographing apparatus shown in FIG. 1.

FIG. 2 shows a circuit for effecting endoscopic photographing by automatic exposure based upon an exposure constant set by selectively operating the push buttons $12_1$ to $12_9$ in the light source unit 12. In the Figure, lamps $L_1$ to $L_9$ are connected to respective switches $SW_1$ to $SW_9$, which are interlocked for their opening and closing to the operation of the respective push buttons $12_1$ to $12_9$. A diode $D_{22}$ is connected between the lamp $L_5$ and switch $SW_5$. These lamps $L_1$ to $L_9$ may be provided, for instance, within covers of the respective push buttons. The switches $SW_1$ to $SW_9$ are also connected through respective diodes $D_1$ to $D_9$ and resistors $R_1$ to $R_9$ to a power supply line $20a$, which is in turn connected through a resistor $R_{10}$ to the positive terminal of a power supply 21. The negative terminal of the power supply 21 is connected through a power supply line $20b$ to the switches $SW_1$ to $SW_9$. Voltage dividing resistors $R_{11}$, $R_{12}$ and $R_{13}$ are connected in series across the power supply 21. The connection point of the voltage dividing resistors $R_{11}$ and $R_{12}$ is connected to an inverting input end of an operational amplifier 22, and the connection point of the voltage dividing resistors $R_{12}$ and $R_{13}$ is connected to a non-inverting input end of an operational amplifier 23. A non-inverting input end of the operational amplifier 22 and an inverting input end of the operational amplifier 23 are connected to the power supply line $20a$. The output ends of the operational amplifiers 22 and 23 are connected through respective forward polarity diodes $D_{20}$ and $D_{21}$ to an oscillator 24. The output end of the oscillator 24 is connected through an alarm signal generating circuit 25 to an alarm loudspeaker 26 and also connected to the base of a transistor 27. The transistor 27 has its collector connected to the positive terminal of a power supply 28 and also has its emitter connected to the lamps $L_1$ to $L_9$ through respective diodes $D_{11}$ to $D_{19}$. The negative terminal of the power supply 28 is connected to the power supply line $20b$.

The output end of the operational amplifier 22 is also connected through a resistor $R_{14}$ to the base of a transistor 29. The line $20b$ is connected through the collector-emitter path of the transistor 29 to the juncture between the switch $SW_5$ and lamp $L_5$. The output end of the operational amplifier 22 is also connected to a control input end of an electronic switch 30. The electronic switch 30 is connected in parallel with a switch $SW_{15}$, which is included in a group of switches $SW_{11}$ to $SW_{16}$ which are interlocked to the respective switches $SW_1$ to $SW_9$. These switches $SW_{11}$ to $SW_{19}$ are individually connected at one end through respective resistors $R_{15}$ to $R_{23}$ to the output end of an operational amplifier 31 and at the other end to one input terminal of an operational amplifier 33 in an integrating circuit 32. The resistors $R_{15}$ to $R_{23}$ have geometrically reducing resistances in the mentioned order; for example, these resistance values are set such that $R_{15}=2R_{16}=4R_{17}=8R_{18}=\ldots$. A capacitor $C_1$ and a switch $SW_{20}$ are connected in parallel between the above-mentioned one input end and the output end of the operational amplifier 33. The integrating circuit 32 is constructed such that its integration constant is variable according to the selection of the resistors $R_{15}$ to $R_{23}$ by the switches $SW_{11}$ to $SW_{19}$, and its output end is connected through a resistor $R_{24}$ to one input end of an operational amplifier 34. A reference voltage source 35 is also connected through resistors $R_{25}$ and $R_{26}$ to this input end of operational amplifier 34. An electronic switch 36 is connected in parallel with the resistor $R_{25}$, and its control input end is connected to the output end of the operational amplifier 23 so that its opening and closing are controlled by the output of the operational amplifier 23. The other input end of the operational amplifier 34 is connected to the other input end of the operational amplifier 33 and also to one output end of a light-receiving element 39 (e.g. photodiode or phototransistor) provided in endoscope 38. The output end of the operational amplifier 34 is connected to a solenoid energizing circuit 37, which has its output end connected to a solenoid 43 of a shutter unit 42 provided between a light source 40 and the light incidence end of a light guide 41 of endoscope 38.

When taking an endoscopic picture with the endoscope 38, to which the light source unit including the circuit described above is connected, one of the push buttons of the light source unit for a corresponding kind of film 45 loaded in the photographic attachment 44 is depressed. When the push button $12_1$, for instance, is depressed, the switch $SW_1$ is closed, whereupon the lamp $L_1$ is turned on to indicate that the push button $12_1$ is correctly depressed. Thereafter, a shutter release button of the attachment is depressed to release the shutter 42, whereby light from the light source 40 is transmitted through a light guide 41 to the body cavity. The transmitted light is reflected by a membrane of the body cavity, and the reflected light is transmitted through an image guide 46, a beam splitter 47, an eyepiece 48 and an aperture of shutter 49 to effect exposure of the film 45. At this time, part of the reflected light is coupled through the beam splitter 47 to the light-receiving element 39. The light-receiving element 39 produces a photocurrent corresponding to an amount of received light, and this photocurrent is converted by a resistor 51 into a voltage which is coupled to an amplifying circuit constituted by the operational amplifier 31 and resistors $R_{27}$ and $R_{28}$. The output of the amplifying circuit is integrated according to the integration constant determined by the resistor $R_{15}$ selected by the switch $SW_{11}$ interlocked to the switch $SW_1$ and the capacitor $C_1$. The integration is thus effected according to the exposure constant corresponding to the kind of film used. The output of the integrating circuit is fed to a level detecting circuit 50 which is constituted by the resistors $R_{24}$, $R_{25}$ and $R_{26}$, electronic switch 36 and operational amplifier 34 and compared with the output of the reference voltage source 35. When the output of the integrating circuit reaches a predetermined value, the solenoid energizing circuit 37 is rendered operative by the output of the operational amplifier 34, thus closing the shutter of the shutter unit 42. In this way, proper exposure of the film 45 is obtained.

While the above operation of the circuit concerns the case when one push button is correctly depressed, now the case of taking a picture without operation of any push button at all will be described. In this case, no current is caused through the resistor $R_{10}$, so that the non-inverting input end of the operational amplifier 22 and the inverting input end of the operational amplifier 23 are brought to a high potential, that is, the output of the operational amplifier 22 is brought to a high level while the output of the operational amplifier 23 is brought to a low level. With the high level output signal of the operational amplifier 22 the electronic switch 30 is closed. Also, with the high level output signal of the operational amplifier 22 the transistor 29 is triggered, so that the lamp $L_5$ is shunted to the line 20b. Further, at this time oscillation of the oscillator 24 is caused so that the output thereof is coupled through the alarm signal generating circuit 25 to cause the loudspeaker 26 to produce an alarm sound while also causing intermittent on-off operation of the transistor 27 to cause blinking of the lamp $L_5$. With the closure of the electronic switch 30, which is connected in parallel with the switch $SW_{15}$, the resistor $R_{19}$ connected thereto is connected to the integrating circuit 32. The resistor $R_{19}$ corresponds to an intermediate one of the selectable exposure constants. In this way, when none of the push buttons is depressed, the photographing is effected according to the intermediate one of the selectable exposure constants, i.e., the exposure constant corresponding to the push button $12_5$.

Now, the case when two adjacent push buttons, for instance, push buttons $12_1$ and $12_2$, are depressed at one time will be described. In this case, currents flow through the resistors $R_1$ and $R_2$, so that a large voltage drop is produced across the resistor $R_{10}$. Thus, the operational amplifier 22 produces a low level output while the operational amplifier 23 produces a high level output. With the high level output signal of the operational amplifier 23 the oscillator 24 is rendered operative, causing the loudspeaker 26 to produce the alarm sound and also causing intermittent on-off operation of the transistor 27 so as to cause blinking of the lamps $L_1$ and $L_2$. Since the switches $SW_{11}$ and $SW_{12}$ are both closed, the integration constant of the integrating circuit is determined in this case by the resultant resistance of the parallel resistors $R_{15}$ and $R_{16}$ and capacitor $C_1$. This integration constant, however, is quite different from the proper exposure constant, and thus appropriate correction of the constant is necessary at this time. In this embodiment, the correction is made such as to obtain a value of the constant intermediate between the constant determined by the resistor $R_{15}$ and that determined by the resistor $R_{16}$. This intermediate value is equal to $1/\sqrt{2}$ of the constant determined by the resistor $R_{15}$, and to obtain this value it is necessary to multiply the reference voltage coupled to the operational amplifier 34 by $3/\sqrt{2}$. In the instant embodiment, instead of multiplying the reference voltage by $3/\sqrt{2}$, the resistor $R_{25}$ included in the path of supply of the reference voltage from the reference voltage source 35 to the operational amplifier 34 is short-circuited. In other words, with the output signal from the operational amplifier 23, the electronic switch 36 is closed to short-circuit the resistor $R_{25}$. When the output voltage of the integrating circuit, being compared with $3/\sqrt{2}$ times the reference voltage thus provided, reaches a constant value, i.e., when the extent of exposure reaches a constant value, the output of the operational amplifier 34 is inverted, thus causing the shutter device 42 to block light from the light source 40.

As has been described in the foregoing, according to the invention the photographing can be effected with proper exposure based upon an exposure constant selected by a push button when that push button is correctly depressed, and also automatic exposure can be obtained on the basis of an intermediate one of the preset exposure constants selectable by the respective push buttons in the case when none of these push buttons is depressed and on an intermediate value between two exposure constants selectable by respective two push buttons in the case when these two buttons are depressed at one time. Thus, even if a given push button fails to be depressed or if more than one push button is depressed by mistake, an exposure which is close to the proper exposure can be automatically obtained, and grave failure in photographing can be prevented. While the case when two push buttons are depressed at one time by mistake has been described, it is possible intentionally to depress two push buttons at one time so as to obtain an intermediate exposure constant. Further, while push button switches are used in the above embodiment, the same effects may also be obtained by using other types of switches such as toggle switches and seesaw switches. Further, it is possible to construct a circuit, which permits similar effects to be obtained when more than two push buttons are depressed at one time.

What is claimed is:

1. An automatic exposure photographing apparatus comprising:
   an exposure constant setting circuit including a plurality of exposure constant selection switches respectively corresponding to different exposure constants including high exposure constants, at least one intermediate exposure constant and low exposure constants for selecting a desired one of said exposure constants;
   a switch operation detecting circuit for producing a detection signal when detecting the fact that none of said exposure constant selection switches is operated;
   an automatic exposure constant setting means for automatically setting said exposure constant setting circuit to said intermediate exposure constant in response to the detection signal from said switch operation detecting circuit;
   an exposure calculation circuit for calculating the extent of exposure according to the exposure constant set by said exposure constant setting circuit or by said automatic exposure constant setting means; and
   a means for ending exposure in response to the output of said exposure calculation circuit.

2. An automatic exposure photographing apparatus comprising:
   an exposure constant setting circuit including a plurality of exposure constant selection switches respectively corresponding to different exposure constants including high exposure constants, at least one intermediate exposure constant and low exposure constants for selecting a desired one of said exposure constants;
   a switch operation detecting circuit for producing a detection signal when detecting the fact that at least two of said exposure constant selection switches are operated;
   an automatic exposure constant setting means for automatically setting an exposure constant of a value equal to the average of at least two exposure constants selected by respective exposure constant selection switches in response to the detection signal from said switch operation detection circuit;
   an exposure calculation circuit for calculating the extent of exposure according to the exposure constant set by said exposure constant setting circuit or by said automatic exposure constant setting means; and
   a means for ending exposure in response to the output of said exposure calculation circuit.

3. An automatic exposure photographing apparatus comprising:
   an exposure constant setting circuit including a plurality of exposure constant selection switches respectively corresponding to different exposure constants including high exposure constants, at least one intermediate exposure constant and low exposure constants for selecting a desired one of said exposure constants;
   a switch operation detecting circuit for producing a first signal when detecting the fact that none of said exposure constant setting switches is operated and producing a second signal when detecting the fact that at least two exposure constant selection switches are operated at one time;
   a first means for setting said exposure constant setting circuit to said intermediate exposure constant in response to said first signal from said switch operation detecting circuit;
   a second means for automatically setting an exposure constant of a value equal to the average of the exposure constants selected by the respective exposure constant selection switches in response to said second signal from said switch operation detecting circuit;
   an exposure calculation circuit for calculating the extent of exposure according to the exposure constant set by either said first means or by said second means; and
   a means for ending exposure in response to the output of said exposure calculation circuit.

4. A photographing apparatus according to claim 3, wherein said exposure calculation circuit includes an integrating circuit having a plurality of integrating resistors individually connected to said respective exposure constant selection switches and producing an integration signal, a reference signal source for producing a reference signal, and a comparator connected to said integrating circuit and to said reference signal source for comparing said integration signal and said reference signal.

5. A photographing apparatus according to claim 3, wherein said switch operation detecting circuit includes a plurality of interlocked switches individually interlocked to said respective exposure constant selection switches, a plurality of load elements individually connected to said respective interlocked switches, and means for detecting load current flowing through said load element according to the operation state of said interlocked switches and producing said first and second signals according to the magnitude of said load current.

6. A photographing apparatus according to claim 3, wherein said first means includes a switch element connected in parallel with the exposure constant selection switch for selecting said intermediate exposure constant and being closed in response to said first signal.

7. A photographing apparatus according to claim 3, wherein said second means includes a means connected to said exposure calculation circuit for obtaining the average value of said exposure constants set by said at least two exposure constant selection switches, in response to said second signal.

8. A photographing apparatus according to claim 3, which further comprises an alarm means for producing an alarm sound in response to said first and second signals.

9. A photographing apparatus according to claim 3, wherein said switch operation detecting circuit includes a plurality of light emitting elements corresponding to said respective exposure constants, and means for lighting one of the light emitting elements corresponding to an exposure constant set by said exposure constant setting circuit.

* * * * *